United States Patent [19]

Makino

[11] 4,297,106
[45] Oct. 27, 1981

[54] RAPID METHOD FOR THE MEASUREMENT OF IODINE VALUE

[75] Inventor: Akira Makino, Yokosuka, Japan

[73] Assignee: The Nisshin Oil Mills, Ltd., Tokyo, Japan

[21] Appl. No.: 174,427

[22] Filed: Aug. 1, 1980

[30] Foreign Application Priority Data

Aug. 2, 1979 [JP] Japan .................................. 54/98127

[51] Int. Cl.³ ............................................. G01N 31/00
[52] U.S. Cl. ............................. 23/230 HC; 23/230 M
[58] Field of Search ......... 23/230 R, 230 HC, 230 M; 422/68, 75; 252/408

[56] References Cited

PUBLICATIONS

Welcher, F. J., editor, *Standard Methods of Chemical Analysis*, D. Van Nostrand Co., Inc., New York, 6th edition, vol. 2, pp. 475-478 and 1438-1441.

Kratochvil, Ryon et al., Analytical Chemistry, vol. 48, No. 3 (Mar. 1976), pp. 568-570.

Morrison, R. T. et al., *Organic Chemistry*, Allyn and Bacon, Inc., Boston, third edition, 1973, pp. 503-505.

*Primary Examiner*—William F. Smith
*Assistant Examiner*—Chris Konkol
*Attorney, Agent, or Firm*—Sughrue, Mion, Zinn, Macpeak & Seas

[57] ABSTRACT

In the measurement of iodine value by the Wijs method, the measurement can be effected rapidly by using magnesium acetate or sodium acetate as a catalyst.

When the catalyst is used, the reaction time of a sample with a Wijs solution is as short as about 3 minutes. The time required for the measurement is thus reduced remarkably.

3 Claims, No Drawings

RAPID METHOD FOR THE MEASUREMENT OF IODINE VALUE

BACKGROUND OF THE INVENTION

The present invention relates to a novel, rapid method for the measurement of iodine value.

Iodine value is measured generally be the Wijs method. This method has, however, a defect that time of the reaction of a sample with the Wijs solution is as long as 30-60 minutes. To achieve a reduction in the reaction time, there has been known a rapid measurement method wherein mercuric acetate is used as a catalyst. However, mercuric acetate which is poisonous must not be detectable in waste water according to the Water Pollution Prevention Law. Further, the storage and the use of mercuric acetate are strictly controlled according to the Special Chemical Regulation Law. Thus, mercuric acetate causes problems of environmental pollution and safety.

SUMMARY OF THE INVENTION

The present invention provides a rapid method for the measurement of iodine value, which is free of the above defects. More particularly, the present invention provides a rapid method for the measurement of iodine value according to the Wijs method, characterized in that magnesium acetate or sodium acetate is used as a catalyst.

DETAILED DESCRIPTION OF THE INVENTION

The magnesium acetate or sodium acetate is used in the form of a solution in glacial acetic acid, preferably having a concentration of 3-5 wt. %.

In carrying out the method of the present invention, the Wijs solution is added to a sample in an ordinary manner and then a solution of the catalyst in glacial acetic acid is added thereto. It is sufficient to use the solution in a quantity of about 5 ml. The reaction time may be as short as about 3 minutes. Then, the iodine value is measured in the same manner as in the Wijs method.

The advantages obtained with the present invention are as shown below:

(1) The iodine value can be measured within the same analysis time as in the case of using mercuric acetate, since the reaction time of a sample with the Wijs solution is as short as about three minutes. The analysis time is thus remarkably shortened.
(2) Magnesium acetate and sodium acetate are not designated as poisons or deadly poisons and can be handled safely.
(3) Measurement accuracy and reproducibility are extremely high.
(4) The method of the invention is advantageous from the viewpoint of the prevention of environmental pollution.
(5) Since the Wijs solution acts rapidly, it can be used as a catalyst solution for an automatic titrimetric analyzer.

The following examples illustrate the present invention.

EXAMPLE 1

Iodine values of various oils and fats were measured by using 5 ml of a 3% solution of magnesium acetate in glacial acetic acid in an ordinary manner, the reaction time being 3 minutes. For comparison, iodine values of the same samples were measured by the conventional Wijs method, the reaction time being 30-60 minutes.

The results are shown in Table 1.

TABLE 1

| Sample | Wijs method | Method of the invention | |
|---|---|---|---|
| | | I | II |
| Linseed oil | 196.6 | 196.2 | 195.8 |
| Safflower oil | 144.3 | 143.9 | 144.1 |
| Soybean oil | 130.6 | 130.0 | 129.9 |
| Rapeseed oil | 116.5 | 116.0 | — |
| Hardened Soybean oil | 72.5 | 72.2 | — |
| Palm oil | 53.1 | 53.1 | 53.1 |
| Coconut oil | 8.5 | 8.4 | 8.4 |

EXAMPLE 2

Iodine values of various oils and fats were measured by using 5 ml of a 5% solution of sodium acetate in glacial acetic acid in an ordinary manner, the reaction time being 3 minutes. For comparison, iodine values of the same samples were measured by the conventional Wijs method, the reaction time being 30-60 minutes.

The results are shown in Table 2.

TABLE 2

| Sample | Wijs method | Method of the invention |
|---|---|---|
| Linseed oil | 195.3 | 194.5 |
| Soybean oil | 131.7 | 130.8 |
| Hardened Soybean oil | 79.6 | 79.2 |
| Coconut oil | 8.4 | 8.2 |

In a book entitled "Standard Analytical Test Methods for Oils and Fats" edited by Nihon Yukagaku Kyokai, there is given a comparison between the conventional rapid method wherein the solution of mercuric acetate in glacial acetic acid is used, and the Wijs method, which reads as shown in Table 3.

TABLE 3

| Sample | Wijs method | Rapid method (wherein mercuric acetate is used) | | |
|---|---|---|---|---|
| | | I | II | III |
| Soybean oil | 131.1 | 130.8 | 131.7 | 132.1 |
| Tsubaki oil | 81.8 | 81.1 | 80.6 | 81.0 |
| Castor oil | 86.1 | 86.7 | 86.7 | 85.7 |
| Refined beef tallow | 45.2 | 45.9 | 45.0 | 45.0 |
| Refined coconut oil | 7.6 | 7.7 | 7.7 | 7.7 |
| Lightly hardened oil | 40.4 | 39.7 | 39.4 | 40.3 |

It is apparent from the above Table that according to the conventional rapid method, the values are distributed below and above the values obtained by the Wijs method. On the other hand, the values obtained by the method of the present invention are not significantly different from those obtained by the Wijs method, no difference lying between them or the difference being only slight as shown in Tables 1 and 2. With respect to the measurement accuracy and reproducibility, the method of the present invention is equivalent or superior to the conventional rapid method.

What is claimed is:

1. A rapid method for the measurement of iodine value according to the Wijs method wherein reaction is greatly reduced by means of a catalyst selected from the group consisting of magnesium acetate or sodium acetate.

2. A method according to claim 1 wherein magnesium acetate or sodium acetate is used in the form of 3-5 wt. % solution thereof in glacial acetic acid.

3. A method as claimed in any of claims 1 or 2 wherein the use of said catalyst enables the reaction time to be as short as about 3 minutes.

* * * * *